(12) United States Patent
Kim et al.

(10) Patent No.: US 7,799,830 B2
(45) Date of Patent: Sep. 21, 2010

(54) CINNAMIC ACID DIMERS, THEIR PREPARATION AND THE USE THEREOF FOR TREATING NEURODEGENERATIVE DISEASE

(75) Inventors: Dong-Jin Kim, Seoul (KR); Kye-Jung Shin, Seoul (KR); Jaehoon Yu, Seoul (KR); Hee-Sul Lee, Seoul (KR)

(73) Assignees: Korea Institute of Science and Technology, Seoul (KR); Scigenic Co., Ltd., Seoul (KR)

( * ) Notice: Subject to any disclaimer, the term of this patent is extended or adjusted under 35 U.S.C. 154(b) by 27 days.

(21) Appl. No.: 10/515,560

(22) PCT Filed: Jun. 25, 2002

(86) PCT No.: PCT/KR02/01209

§ 371 (c)(1),
(2), (4) Date: Nov. 22, 2004

(87) PCT Pub. No.: WO03/099269

PCT Pub. Date: Dec. 4, 2003

(65) Prior Publication Data

US 2005/0203180 A1     Sep. 15, 2005

(30) Foreign Application Priority Data

May 24, 2002   (KR) ............................... 2002-28871

(51) Int. Cl.
*A61K 31/235*   (2006.01)
*A61K 31/19*    (2006.01)
*C07C 69/00*    (2006.01)
*C07C 229/00*   (2006.01)
*C07C 62/00*    (2006.01)
*C07C 55/28*    (2006.01)

(52) U.S. Cl. .................. 514/533; 514/570; 560/64; 562/453; 562/465; 562/489

(58) Field of Classification Search .................. 514/533, 514/554, 570; 562/488, 489, 453, 465; 560/64
See application file for complete search history.

(56) References Cited

FOREIGN PATENT DOCUMENTS

| EP | 0198262 A2 | 10/1986 |
|---|---|---|
| JP | 2000136176 | 5/2000 |
| KR | 1020020080686 A | 10/2002 |

OTHER PUBLICATIONS

Kolodynska et al, Synthesis of ferulamide and isoferulamide derivatives, 1973, Acta Poloniae Pharmaceutica, 30 (4), p. 353-9, abstract (p. 1).*
Mo et al, Synthesis of derivatives of ferulic acid, 1985, Yaoxue Xuebao, 20(8), 584-91, abstract page (p. 1).*
Kolodynska and Wieniawski, Acta Pol. Pharm., vol. 30, No. 4, pp. 353-359(1973).
Hay and Klavetter, "Aliphatic Phenylene Vinylene Copolymers: Tuning the Color of Luminescence through Co-monomer Fe", J. Am. Chem. Soc., vol. 117, No. 27, pp. 7112-7118 (1995).

* cited by examiner

*Primary Examiner*—Taylor Victor Oh
(74) *Attorney, Agent, or Firm*—Lucas & Mercanti, LLP

(57) ABSTRACT

The present invention relates to cinnamic acid dimers, their preparation and the use thereof for treating neurodegenerative disease, which have excellent effect on enhancing the learning and memory-retention ability in vivo and have fewer side-effects by showing no hormone properties, even when administered for a long period of time, and thus which can be used for neurodegenerative disease including dementia.

15 Claims, 1 Drawing Sheet

CINNAMIC ACID DIMERS, THEIR PREPARATION AND THE USE THEREOF FOR TREATING NEURODEGENERATIVE DISEASE

TECHNICAL FIELD

The present invention relates to cinnamic acid dimers and their pharmaceutically acceptable salts having excellent effect on enhancing the learning and memory-retention ability in vivo, preparation thereof and their usage for preventing and treating neurodegenerative disease.

BACKGROUND ART

Among various fields of medical science, neurodegenerative diseases have been the least developed. Accordingly, thesesdays many foreign pharmaceutical companies are focusing on neurodegenerative diseases, especially, on dementia. Since no excellent treatment for dementia has been developed yet, the development of a new treatment for dementia is expected to form a huge market.

Upon pathological examination of dementia patients' cerebral cells and organs, plaque formed by the accumulation of β-amyloid protein has been commonly observed. However, it is controversial whether such plaque works as a pathogenesis or is accumulated as a product of the pathogenesis. Only the fact that senile plaques were formed in most dementia patients, and that dementia symptoms improved when such plaques decreased was observed. Many researchers have looked for the cause of dementia and its treatment, but they have not been revealed, yet.

On the other hand, Korean Pat. Application No. 2001-20411 and International Pat. Application No. PCT/KR01/02103 by the present inventors, the content thereof being incorporated herein by reference, disclose excellent therapeutic effects of ferulic acid dimers on dementia. The excellent therapeutic effects of ferulic acid dimers on dementia has been confirmed by an in vivo experiment, wherein ferulic acid dimers are administrated to a mouse, wherein leads to a considerable increase in the memory-retention ability of the mouse. A biochemical mechanism of ferulic acid has not been revealed yet, but the above Pat. Applications, disclose that ferulic acid dimers have excellent therapeutic effects on dementia.

SUMMARY OF THE INVENTION

We, the inventors of the present invention, prepared a novel compound of cinnamic acid dimers showing an improved treatment effect on dementia. The cinnamic acid dimers of the present invention have an improved treatment effect on dementia and minimize the side-effects caused by excessive administration of drugs, by showing no hormone properties.

Accordingly, it is an object of the present invention to provide cinnamic acid dimers, their pharmaceutically acceptable salts, their preparation and the use thereof for preventing and treating neurodegenerative disease.

BRIEF DESCRIPTION OF THE DRAWINGS

The above and other objects, features and other advantages of the present invention will be more clearly understood from the following detailed description taken in conjunction with the accompanying drawing, in which.

Figure 1:
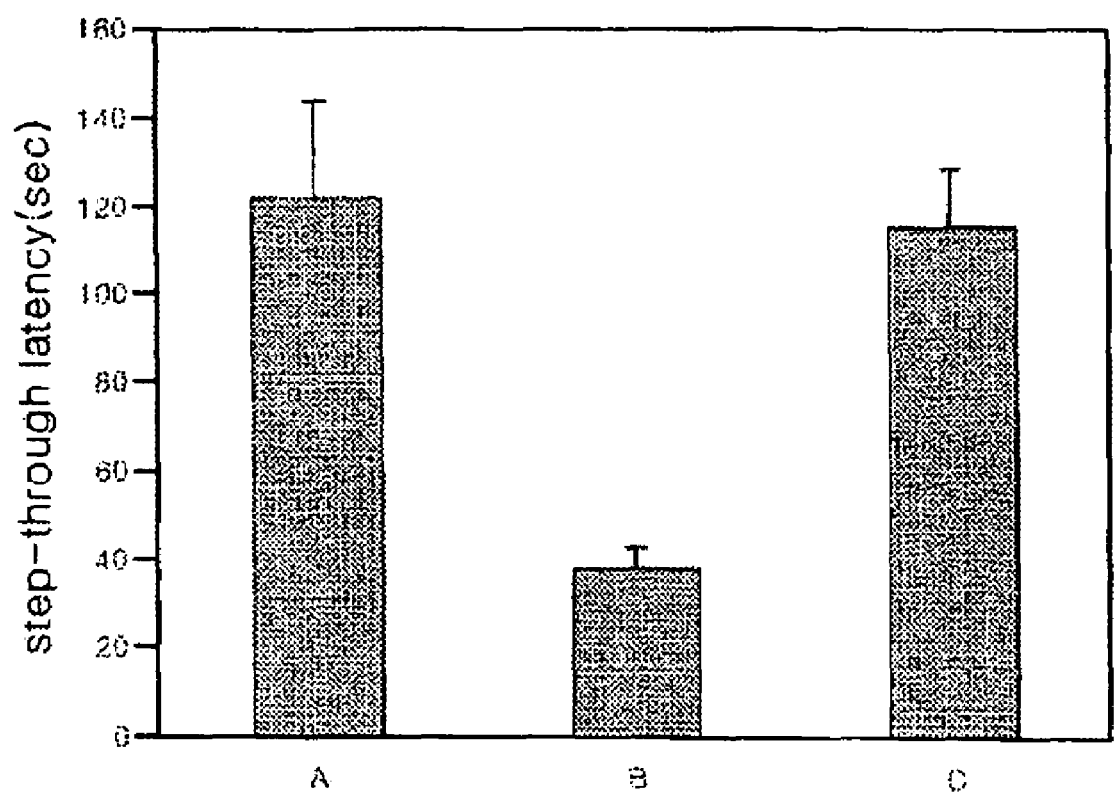
FIG. 1 is a histogram showing the passive avoidance response time of cinnamic acid dimers (example 1) of the present invention.

A is the mice administered with physiological saline solution,

B is the mice administered with beta-amyloid,

C is the mice administered with cinnamic acid dimers (example 1) and beta-amyloid.

DISCLOSURE OF THE INVENTION

To accomplish these objects, the present invention provides cinnamic acid dimers and their pharmaceutically acceptable salts.

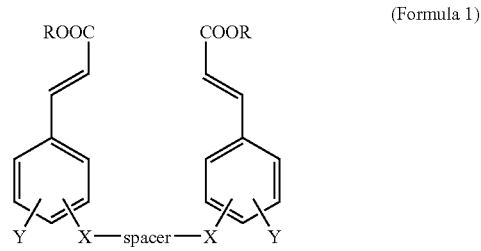

(Formula 1)

wherein, R is hydrogen or alkyl group of $C_1$-$C_3$,

X is oxygen or —NH, —NCH$_3$,

Y is —OCH$_3$, —NHCH$_3$ or —N(CH$_3$)$_2$,

Spacer is carbon, or alkyl group of $C_2$-$C_8$ comprising oxygen or nitrogen,

X and Y of cinnamic acid dimers are in the position of ortho, meta or para.

Cinnamic acid dimers of the present invention can be prepared in a form of inorganic salts, such as sodium salt, potassium salt, magnesium salt and calcium salt; or in a form of organic salts by angelic acid, lysine and ethanolamine, N,N'-dibenzylethylenediamine. Further, the cinnamic acid dimers of the present invention can be prepared as ester forms with triterpene alcohol or plant sterols such as cycloartenol.

Also, the present invention comprises not only cinnamic acid dimers and their pharmaceutically acceptable salts, but also any solvated salt and hydrated salt which can be prepared therefrom.

As can be seen in the following formula 1, cinnamic acid dimers of the present invention have a structure wherein alkoxy group or alkylamine group substituted at a position of ortho, meta or para of each benzene ring comprising the core of each cinnamic acid monomer is connected with chains of suitable lengths, that is, 2-8 carbon containing chains or oxygen or nitrogen-containing chains.

The present invention provides a preparation method of cinnamic acid dimers represented by formula 1 according to reaction scheme 1.

(Reaction scheme 1)

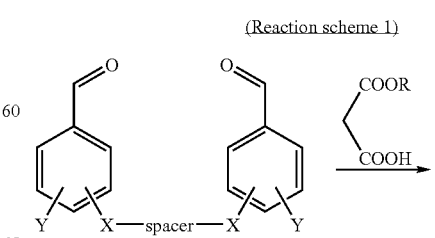

2

-continued

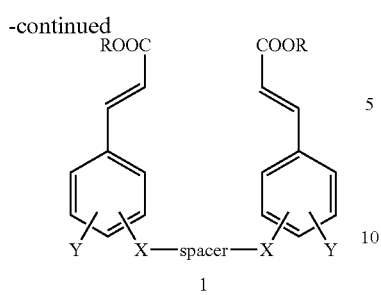

1 wherein, R, X, Y and spacer are defined as above formula 1.

As represented by reaction scheme 1, the preparation method of cinnamic acid dimers (formula 1) of the present invention comprises reacting benzaldehyde dimer compounds of formula 2 with malonic acid or malonic acid ester to obtain cinnamic acid dimers of formula 1.

The reaction, known in the name of "Knoevenagel reaction" is commonly and widely known in the field of organic chemistry, and the reaction condition (usable solvents, reaction temperature and reaction time and so forth) may be appropriately selected, considering reactants and products. In this regard, as a solvent, various alkaline organic solvents including piperidine and pyridine can be used, for example, lutidine, dimethylformamide and so on. Also, the reaction temperature is usually in the range of 80-100° C., and the reaction time ranges commonly from 2 to 6 hours. It is preferred that the reaction is conducted at 80-90° C. for 3-5 hours in the presence of piperidine and pyridine.

In order to prepare cinnamic acid dimers of the present invention, benzaldehyde dimers of formula 2 used as a starting material can be produced according to the method shown in the following reaction scheme 2. More specifically, this can be obtained according to the following step; a hydroxybenzaldehyde compound or aminobenzaldehyde compound of formula 3 is reacted with a ditosyl compound of formula 4 in the presence of base to obtain an bezaldehyde dimer compound of formula 2.

(Reaction scheme 2)

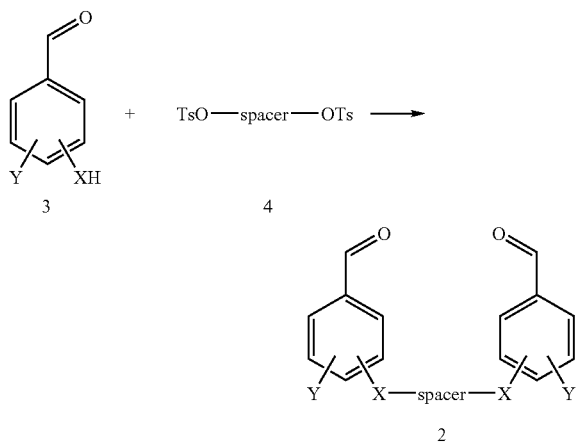

2 wherein, R, X, Y and spacer are defined as above formula 1.

In the preparation method, examples of useful bases include strong alkaline such as LiH, NaH, KH, KOH, NaOH and the like or weak alkaline such as $K_2CO_3$, $Na_2CO_3$ and the like, but are certainly not limited to them.

The present invention provides intermediates represented by formula 2, used in the preparation of cinnamic acid dimers represented by formula 1.

(Formula 2)

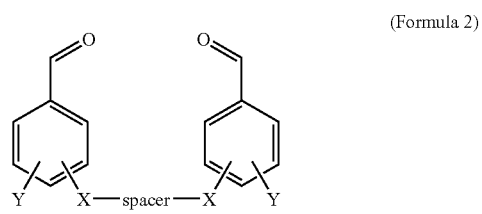

wherein, R, X, Y and spacer are defined as above formula 1.

Also, the present invention provides a pharmaceutical composition for preventing and treating neurodegenerative disease comprising cinnamic acid dimers and their pharmaceutically acceptable salts.

The cinnamic acid dimers of the present invention have an excellent effect on treating neurodegenerative disease. Particularly, as a result of the step-through latency by the passive avoidance test on mice (FIG. 1), the step-through latency(sec) for the mice administered with both cinnamic acid dimers of formula 1 and beta-amyloid is the same as that of the control mice administered with physiological saline solution and is significantly higher than that of the control mice administered with beta-amyloid only. As shown from the results, it has been found out that cinnamic acid dimers have an excellent effect on enhancing the learning and memory-retention ability, and can be used for preventing and treating neurodegenerative disease, such as dementia. Also, cinnamic acid dimers have fewer side-effects by showing no hormone properties, even when administered for a long period of time.

According to the general methods, cinnamic acid dimers of the present invention can be mixed with suitable carrier or vehicles, or diluted with diluents to produce pharmaceutical compositions for preventing and treating neudegenerative disease. Suitable carriers, vehicles and diluents include lactose, dextrose, sucrose, sorbitol, mannitol, xylitol, erythritol, maltitol, starches, acacia gum, algimates, gelatin, calcium phosphate, calcium silicate, cellulose, methylcellulose, microcrystalline cellulose, polyvinylpyrolidone, water, methyl hydroxy benzoates, propylhydroxybenzoates, talc, magnesium stearate and mineral oil. The pharmaceutical compositions further include fillers, antiagglutinant, lubricant, moistening agent, aromatics, emulsifiers, preservatives, etc. The compositions of the present invention can be prepared in a dosage form using methods well known in the art to provide fast, continuous or sustained release of active ingredients after being administered to mammals. The dosage form may be a tablet, pill, powder, sachet, elixir, suspension, emulsion, solution, syrup, aerosol, soft or hard gelatin capsule, sterile injectable solution, or sterile packaged powder.

The pharmaceutical composition of the present invention may be administered through various routes including oral, or transdermal, subcutaneous, intravenous or intramuscular introduction. A preferable daily dose may range from 10 to 30 mg/kg of the body weight, and can be administered in a single dose or in separate doses. However, it should be understood by anyone skilled in the art that the amount of the active being ingredient actually administered ought to be determined in light of various relevant factors including the chosen route of administration, the age, sex and body weight of the individual subject, and the severity of the subject's symptoms; and therefore, the above dose should not be construed to limit the scope of the present invention in any way.

As a result of the acute toxic test of cinnamic acid dimers of the present invention on mice, it has been found out that cinnamic acid dimers have high biostability showing an $LD_{50}$ above 5,000 mg/kg without showing acute toxicity at all, and therefore, the compound of the present invention can be safely administered in organisms.

EXAMPLE

Example 1

Preparation of 1,2-di[2-methoxy-4-(2-carboxylvinyl)]phenoxyethane (step 1) Preparation of 1,2-di(2-methoxy-4-formyl)phenoxyethane 5 g (32.8 mmol) of 3-methoxy-4-hydroxybenzaldehyde was dissolved in 200 ml of anhydrous dimethylformamide, and then 1.58 g (39.4 mmol) of 60% NaH was slowly added at room temperature. The reaction mixture was stirred at this temperature for 30 minutes, wherein 5.78 g (15.6 mmol) of ethyleneglycol ditosylate was added after certifying that gas has stopped being generated. The reaction mixture was stirred at 80° C. for 5 hours, and then cooled at room temperature after the completion of reaction was confirmed using thin layer chromatography (TLC), then the reaction mixture was added to 1000 ml of water and stirred vigorously. The produced solid compound was filtered, washed with 1000 ml of water and 500 ml of hexane, and then dried in a vacuum dryer, to yield 4.86 g (94.1%) of 1,2-[2-(para-methoxybenzyloxy)-5-formyl]phenoxyethane, as white solid.

$^1$H NMR (300 MHz, DMSO) δ 9.86(s, 2H), 7.57(dd, 2H, J=1.8, 8.2 Hz), 7.41(d, J=1.8 Hz, 2H), 7.27(d, 2H, J=8.2 Hz), 4.48(s, 4H), 3.82(s, 6H).

(step 2) Preparation of 12-di[2-methoxy-4-(2-carbonylvinyl)]phenoxyethane 5.66 g (17.1 mmol) of the 1,2-di(2-methoxy-4-formyl)phenoxyethane, prepared in step 1, and 8.92 g (85.6 mmol) of malonic acid were fully dissolved in 70 ml of anhydrous pyridine, and then added with 0.5 ml of piperidine. The reaction mixture was stirred at 80° C. for 8 hours, and then cooled at room temperature after the completion of reaction had been confirmed, followed by filtering the produced crystals. The crystals were continuously washed with 500 ml of ethanol and 500 ml of ether, and then dried in the vacuum dryer, to obtain 6.97 g (98.1%) of 1,2-di[2-methoxy-4-(2-carboxylvinyl)]phenoxyethane, as white crystals.

$^1$H NMR (300 MHz, DMSO) δ 12.1(bs, 2H), 7.44(d, 2H, J=15.8 Hz), 7.24(s, 2H), 7.12(d, 2H, J=8.2 Hz), 6.95(d, 2H, J=8.2 Hz), 6.38(d, 2H, J=15.8 Hz), 4.24(s, 4H), 3.70(s, 6H); $^{13}$C NMR (75 MHz, DMSO) δ 168.79, 150.55, 149.83, 144.93, 128.28, 123.44, 117.77, 113.53, 111.38, 67.84, 56.39;

IR(KBr) 2954, 1692, 1512, 1260 cm$^{-1}$;

Anal. Calcd for $C_{22}H_{22}O_8$: C, 63.76; H, 5.35. Found: C, 63.4; H, 5.4.

Example 2

Preparation of Cinnamic Acid Dimers of Present Invention

Various cinnamic acid dimers were prepared according to the same procedure as example 1. The results are shown in tables 1, 2, 3, 4.

TABLE 1

| Structure | NMR data |
|---|---|
| [Chemical structure: HOOC-CH=CH-(3-OCH₃-phenyl)-O-(CH₂)₃-O-(3-OCH₃-phenyl)-CH=CH-COOH] | 12.22(bs, 2H), 7.51(d, 2H, J=15.8Hz), 7.32(d, 2H, J=1.6Hz), 7.18(dd, 2H, J=1.6, 8.4Hz), 7.01(d, 2H, J=8.4Hz), 6.44(d, 2H, J=15.8Hz), 4.15(t, 4H, J=6.1Hz), 3.81(s, 6H), 2.18(t, 2H, J=6.1Hz). |
| [Chemical structure: HOOC-CH=CH-(3-OCH₃-phenyl)-O-CH₂-CH=CH-CH₂-O-(3-OCH₃-phenyl)-CH=CH-COOH] | 12.17(bs, 2H), 7.45(d, 2H, J=15.8Hz), 7.25(s, 2H), 7.11(d, 2H, J=8.1Hz), 6.91(d, 2H, J=8.1Hz), 6.38(d, 2H, J=15.8Hz), 5.99(s, 2H), 4.55(s, 4H), 3.73(s, 6H). |
| [Chemical structure: HOOC-CH=CH-(3-OCH₃-phenyl)-O-(CH₂)₅-O-(3-OCH₃-phenyl)-CH=CH-COOH] | 12.21(bs, 2H), 7.51(d, 2H, J=15.8Hz), 7.30(d, 2H, J=1.7Hz), 7.17(dd, 2H, J=1.7, 8.4Hz), 6.97(d, 2H, J=8.4Hz), 6.43(d, 2H, J=15.8Hz), 4.00(t, 4H, J=6.3Hz), 3.79(s, 6H), 1.80~1.73(m, 4H), 1.56-1.51(m, 2H). |

TABLE 1-continued

| Structure | NMR data |
|---|---|
| (structure) | 12.20(bs, 2H), 7.51(d, 2H, J=15.9Hz), 7.30(s, 2H), 7.18(d, 2H, J=8.2Hz), 6.96(d, 2H, J=8.2Hz), 6.43(d, 2H, J=15.9Hz), 3.99(t, 4H, J=6.0Hz), 3.79(s, 6H), 1.74(bs, 4H), 1.46(bs, 4H). |
| (structure) | 12.19(bs, 2H), 7.49(d, 2H, J=15.9Hz), 7.29(s, 2H), 7.16(d, 2H, J=8.3Hz), 6.97(d, 2H, J=8.3Hz), 6.43(d, 2H, J=15.9Hz), 4.12(t, 4H, J=4.4Hz), 3.81(t, 4H, J=4.4Hz), 3.78(s, 6H). |
| (structure) | 12.20(bs, 2H), 7.48(d, 2H, J=15.9Hz), 7.29(d, 2H, J=1.5Hz), 7.14(dd, 2H, J=1.5, 8.4Hz), 6.94(d, 2H, J=8.4Hz), 6.42(d, 2H, J=15.9Hz), 4.07(t, 4H, J=4.3Hz), 3.77(s, 6H), 3.72(t, 4H, J=4.3Hz), 3.58(s, 4H). |
| (structure) | 7.50(d, 2H, J=15.8Hz), 7.33(d, 2H, J=1.6H), 7.19(dd, 2H, J=1.6, 8.4Hz), 7.03(d, 2H, J=8.4Hz), 6.41(d, 2H, J=15.8Hz), 4.14(t, 4H, J=6.1Hz), 3.81(s, 6H), 3.72(s, 6H), 2.18(t, 2H, J=6.1Hz). |
| (structure) | 12.18(bs, 2H), 7.53(d, 2H, J=15.9Hz), 7.42(d, 2H, J=1.6Hz), 7.23(dd, 2H, J=1.6, 8.4Hz), 7.00(d, 2H, J=8.4Hz), 6.46(d, 2H, J=15.9Hz), 4.38(s, 4H), 3.79(s, 6H). |
| (structure) | 12.20(bs, 2H), 7.51(d, 2H, J=15.8Hz), 7.41(d, 2H, J=1.6Hz), 7.17(dd, 2H, J=1.6, 8.3Hz), 6.99(d, 2H, J=8.3Hz), 6.42(d, 2H, J=15.8Hz), 4.13(t, 4H, J=6.0Hz), 3.78(s, 6H), 2.17(t, 2H, J=6.0Hz). |

TABLE 2

| Structure | NMR data |
|---|---|
| (structure) | 12.18(bs, 2H), 7.49(d, 2H, J=15.8Hz), 7.40(s, 2H), 7.16(d, 2H, J=8.2Hz), 6.97(d, 2H, J=8.2Hz), 6.39(d, 2H, J=15.8Hz), 5.97(s, 2H), 4.55(s, 4H), 3.75(s, 6H). |
| (structure) | 12.22(bs, 2H), 7.57(d, 2H, J=15.9Hz), 7.42(d, 2H, J=1.6Hz), 7.17(dd, 2H, J=1.6, 8.3Hz), 6.99(d, 2H, J=8.3Hz), 6.44(d, 2H, J=15.9Hz), 4.01(t, 4H, J=6.2Hz), 3.76(s, 6H), 1.81~1.76(m, 4H), 1.58~1.53(m, 2H). |

TABLE 2-continued

| Structure | NMR data |
|---|---|
| | 12.20(bs, 2H), 7.56(d, 2H, J=15.9Hz), 7.40(d, 2H, J=1.7Hz), 7.18(dd, 2H, J=1.7, 8.3Hz), 6.97(d, 2H, J=8.3Hz), 6.49(d, 2H, J=15.9Hz), 3.92(t, 4H, J=6.1Hz), 3.79(s, 6H), 1.78'8 1.69(m, 4H), 1.52~1.47(m, 4H). |
| 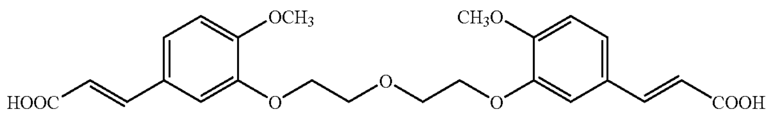 | 12.17(bs, 2H), 7.59(d, 2H, J=15.8Hz), 7.39(s, 2H), 7.19(d, 2H, J=8.4Hz), 6.95(d, 2H, J=8.4Hz), 6.49(d, 2H, J=15.8Hz), 4.02(t, 4H, J=4.3Hz), 3.80(t, 4H, J=4.3Hz), 3.77(s, 6H). |
| 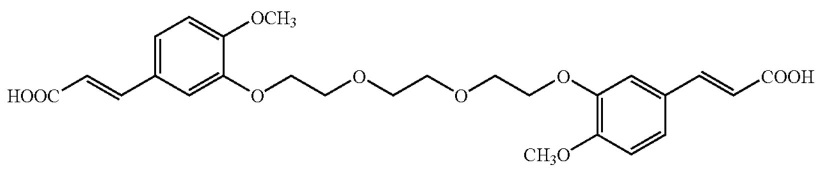 | 12.22(bs, 2H), 7.58(d, 2H, J=15.9Hz), 7.41(d, 2H, J=1.6Hz), 7.17(dd, 2H, J=1.6, 8.4Hz), 6.99(d, 2H, J=8.4Hz), 6.44(d, 2H, J=15.9Hz), 4.02(t, 4H, J=4.4Hz), 3.79(s, 6H), 3.73(t, 4H, J=4.4Hz), 3.52(s, 4H). |
| 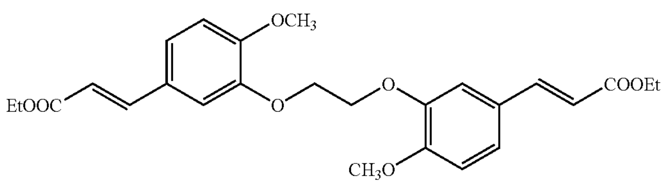 | 7.51(d, 2H, J=15.9Hz), 7.39(d, 2H, J=1.6Hz), 7.21(dd, 2H, J=1.6, 8.4Hz), 6.98(d, 2H, J=8.4Hz), 6.45(d, 2H, J=15.9Hz), 4.36(s, 4H), 4.12 (q, 4H, J=6.2Hz), 3.79(s, 6H), 1.29(t, 6H, J=6.2Hz). |
| 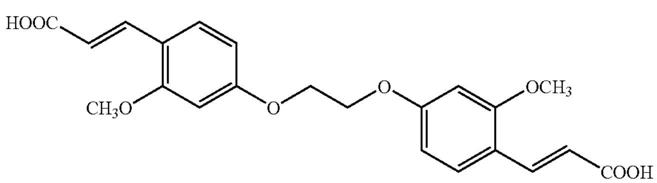 | 12.10(bs, 2H), 7.75(d, 2H, J=16.1Hz), 7.61(d, 2H, J=8.6Hz), 6.61(d, 2H, J=2.3Hz), 6.57(dd, 2H, J=2.3, 8.6Hz), 6.37(d, 2H, J=16.1Hz), 4.21(s, 4H), 3.80(s, 6H) |
| 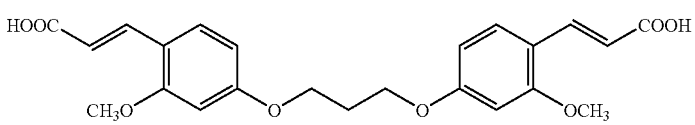 | 12.12(bs, 2H), 7.72(d, 2H, J=16.0Hz), 7.57(d, 2H, J=8.5Hz), 6.58(dd, 2H, J=2.2, 8.5Hz), 6.55(d, 2H, J=8.5Hz), 6.35(d, 2H, J=16.0Hz), 4.12(t, 4H, J=6.1Hz), 3.81(s, 6H), 2.17(t, 2H, J=6.1Hz). |
| 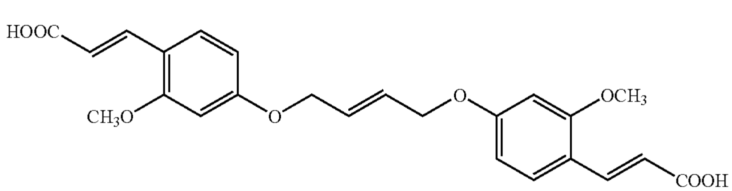 | 12.17(bs, 2H), 7.75(d, 2H, J=15.9Hz), 7.55(s, 2H), 6.59(d, 2H, J=8.4Hz), 6.57(d, 2H, J=8.4Hz), 6.38(d, 2H, J=15.9Hz), 6.02(s, 2H), 4.57(s, 4H), 3.78(s, 6H). |
| 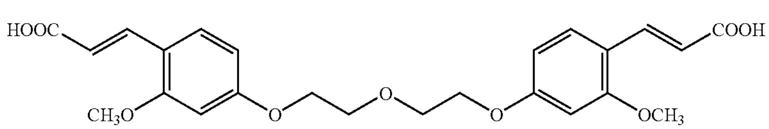 | 12.13(bs, 2H), 7.79(d, 2H, J=16.1Hz), 7.59(s, 2H), 6.62(d, 2H, J=8.6Hz), 6.58(d, 2H, J=8.6Hz), 6.39(d, 2H, J=16.1Hz), 4.07(t, 4H, J=4.2Hz), 3.81(t, 4H, J=4.2Hz), 3.79(s, 6H). |

TABLE 2-continued

| Structure | NMR data |
|---|---|
| 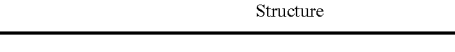 | 12.10(bs, 2H), 7.78(d, 2H, J=16.1Hz), 7.58(d, 2H, J=2.2Hz), 6.60(dd, 2H, J=2.2, 8.6Hz), 6.56(d, 2H, J=8.6Hz), 6.36(d, 2H, J=16.1Hz), 4.11(t, 4H, J=4.3Hz), 3.80(s, 6H), 3.74(t, 4H, J=4.3Hz), 3.58(s, 4H). |

TABLE 3

| Structure | NMR data |
|---|---|
| 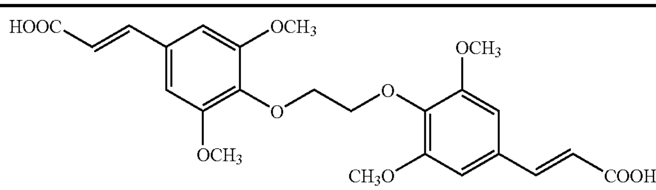 | 12.16(bs, 2H), 7.43(d, 2H, J=15.9Hz), 6.94(s, 2H), 6.45(d, 2H, J=15.9Hz), 4.04(s, 4H), 3.71(s, 6H). |
| 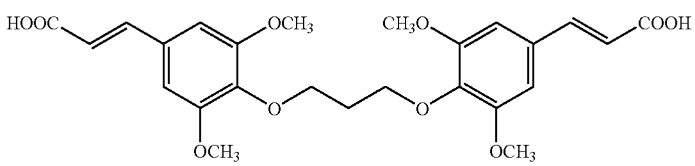 | 12.21(bs, 2H), 7.45(d, 2H, J=15.8Hz), 6.95(2, 2H), 6.44(d, 2H, J=15.8Hz), 4.12(t, 4H, J=6.0Hz), 3.73(s, 6H), 2.16(t, 2H, J=6.0Hz). |
| 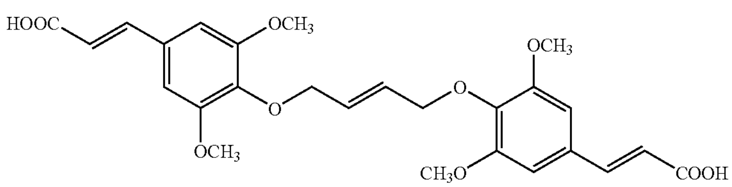 | 12.18(bs, 2H), 7.45(d, 2H, J=15.8Hz), 6.97(s, 2H), 6.40(d, 2H, J=15.8Hz), 5.92(s, 2H), 4.51(s, 4H), 3.73(s, 6H). |
| 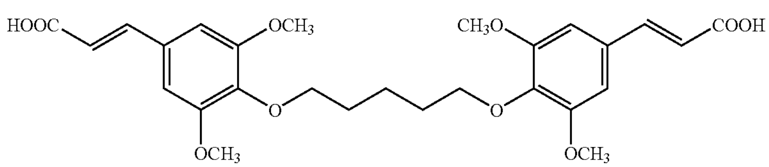 | 12.21(bs, 2H), 7.47(d, 2H, J=15.9Hz), 6.96(s, 2H), 6.43(d, 2H, J=15.9Hz), 3.99(t, 4H, J=6.2Hz), 3.72(s, 6H), 1.81~1.75(m, 4H), 1.55~1.49(m, 2H). |
| 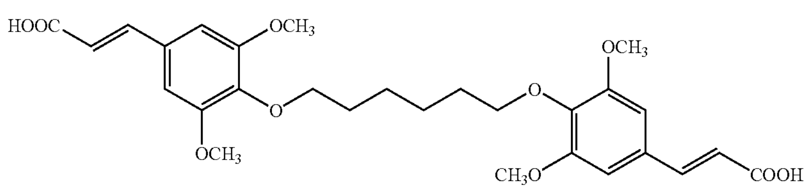 | 12.19(bs, 2H), 7.42(d, 2H, J=15.8Hz), 6.92(s, 2H), 6.43(d, 2H, J=15.8Hz), 3.90(t, 4H, J=6.0Hz), 3.73(s, 6H), 1.78~1.71(m, 4H), 1.49~1.40(m, 4H). |
| | 12.21(bs, 2H), 7.41(d, 2H, J=15.9Hz), 6.93(s, 2H), 6.41(d, 2H, J=15.9Hz), 4.03(t, 4H, J=4.2Hz), 3.79(t, 4H, J=4.2Hz), 3.71(s, 6H). |
| 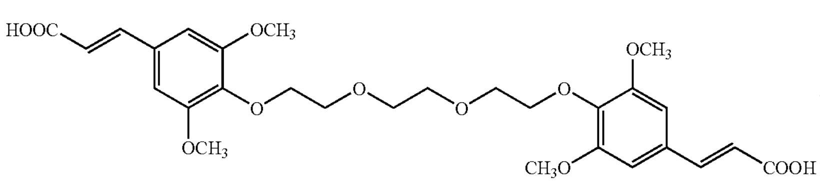 | 12.20(bs, 2H), 7.43(d, 2H, J=15.8Hz), 6.92(s, 2H), 6.42(d, 2H, J=15.8Hz), 4.01(t, 4H, J=4.1Hz), 3.73(s, 6H), 3.71(t, 4H, J=4.1Hz), 3.57(s, 2H). |

TABLE 3-continued

| Structure | NMR data |
|---|---|
| (structure: HOOC-CH=CH-[phenyl with NHCH₃]-O-CH₂-CH₂-O-[phenyl with NHCH₃]-CH=CH-COOH) | 12.21(bs, 2H), 7.53(d, 2H, J=15.8Hz), 7.30(s, 2H), 7.15(d, 2H, J=8.2Hz), 7.03(d, 2H, J=8.2Hz), 6.45(d, 2H, J=15.8Hz), 4.30(bs, 2H), 4.11(s, 2H), 2.94(s, 6H). |
| (structure: HOOC-CH=CH-[phenyl with NHCH₃]-O-(CH₂)₃-O-[phenyl with NHCH₃]-CH=CH-COOH) | 12.22(bs, 2H), 7.51(d, 2H, J=15.8Hz), 7.34(s, 2H), 7.12(d, 2H, J=8.3Hz), 7.01(d, 2H, J=8.3Hz), 6.42(d, 2H, J=15.8Hz), 4.92(bs, 2H), 4.12(t, 4H, J=6.2Hz), 3.03(s, 6H), 2.12(t, 2H, J=6.2Hz). |
| (structure: HOOC-CH=CH-[phenyl with N(CH₃)₂]-O-CH₂-CH₂-O-[phenyl with N(CH₃)₂]-CH=CH-COOH) | 12.17(bs, 2H), 7.54(d, 2H, J=15.8Hz), 7.29(s, 2H), 7.13(d, 2H, J=8.4Hz), 7.01(d, 2H, J=8.4Hz), 6.43(d, 2H, J=15.8Hz), 4.15(s, 4H), 3.07(s, 12H). |

TABLE 4

| Structure | NMR data |
|---|---|
| (structure: HOOC-CH=CH-[phenyl with N(CH₃)₂]-O-(CH₂)₃-O-[phenyl with N(CH₃)₂]-CH=CH-COOH) | 12.16(bs, 2H), 7.55(d, 2H, J=15.9Hz), 7.31(s, 2H), 7.11(d, 2H, J=8.4Hz), 7.03(d, 2H, J=8.4Hz), 6.45(d, 2H, J=15.9Hz), 4.09(t, 4H, J=6.2Hz), 3.09(s, 12H), 2.15(t, 2H, J=6.2Hz). |
| (structure: HOOC-CH=CH-[phenyl with NHCH₃]-O-CH₂-CH₂-O-[phenyl with CH₃HN]-CH=CH-COOH) | 12.18(bs, 2H), 7.53(d, 2H, J=15.9Hz), 7.41(s, 2H), 7.22(d, 2H, J=8.3Hz), 6.97(d, 2H, J=8.3Hz), 6.43(d, 2H, J=15.9Hz), 4.31(s, 4H), 4.03(bs, 2H), 3.11(s, 6H). |
| (structure: HOOC-CH=CH-[phenyl with NHCH₃]-O-(CH₂)₃-O-[phenyl with HNCH₃]-CH=CH-COOH) | 12.15(bs, 2H), 7.51(d, 2H, J=15.8Hz), 7.43(s, 2H), 7.19(d, 2H, J=8.3Hz), 6.92(d, 2H, J=8.3Hz), 6.45(d, 2H, J=15.8Hz), 4.33(bs, 2H), 4.18(t, 4H, J=6.1Hz), 3.17(s, 6H), 2.13(t, 2H, J=6.1Hz). |
| (structure: HOOC-CH=CH-[phenyl with N(CH₃)₂]-O-CH₂-CH₂-O-[phenyl with N(CH₃)₂]-CH=CH-COOH) | 12.21(bs, 2H), 7.55(d, 2H, J=15.9Hz), 7.39(s, 2H), 7.24(d, 2H, J=8.4Hz), 6.96(d, 2H, J=8.4Hz), 6.42(d, 2H, J=15.9Hz), 4.33(s, 4H), 3.04(s, 12H). |
| (structure: HOOC-CH=CH-[phenyl with N(CH₃)₂]-O-(CH₂)₃-O-[phenyl with N(CH₃)₂]-CH=CH-COOH) | 12.15(bs, 2H), 7.51(d, 2H, J=15.8Hz), 7.43(s, 2H), 7.19(d, 2H, J=8.3Hz), 6.92(d, 2H, J=8.3Hz), 6.45(d, 2H, J=15.8Hz), 4.18(t, 4H, J=6.1Hz), 3.17(s, 12H), 2.13(t, 2H, J=6.1Hz). |

TABLE 4-continued

| Structure | NMR data |
|---|---|
| HOOC-CH=CH-C6H2(OCH3)-NH-CH2CH2-NH-C6H2(OCH3)-CH=CH-COOH | 12.20(bs, 2H), 7.59(d, 2H, J=15.8Hz), 7.35(s, 2H), 7.19(d, 2H, J=8.4Hz), 6.92(d, 2H, J=8.4Hz), 6.47(d, 2H, J=15.8Hz), 4.20(bs, 2H), 3.74(s, 6H), 3.16(s, 4H). |
| HOOC-CH=CH-C6H2(OCH3)-N(CH3)-CH2CH2-N(CH3)-C6H2(OCH3)-CH=CH-COOH | 12.15(bs, 2H), 7.55(d, 2H, J=15.9Hz), 7.31(s, 2H), 7.17(d, 2H, J=8.4Hz), 6.90(d, 2H, J=8.4Hz), 6.45(d, 2H, J=15.9Hz), 3.77(s, 6H), 3.17(s, 4H), 3.11(s, 6H). |
| HOOC-CH=CH-C6H2(OCH3)-NH-CH2CH2CH2-NH-C6H2(OCH3)-CH=CH-COOH | 12.22(bs, 2H), 7.57(d, 2H, J=15.8Hz), 7.33(s, 2H), 7.19(d, 2H, J=8.4Hz), 6.91(d, 2H, J=8.4Hz), 6.45(d, 2H, J=15.8Hz), 4.13(bs, 2H), 3.79(s, 6H), 3.13(t, 4H, J=6.2Hz), 2.13(t, 2H, J=6.2Hz). |
| HOOC-CH=CH-C6H2(OCH3)-N(CH3)-CH2CH2CH2-N(CH3)-C6H2(OCH3)-CH=CH-COOH | 12.18(bs, 2H), 7.53(d, 2H, J=15.9Hz), 7.31(s, 2H), 7.18(d, 2H, J=8.3Hz), 6.92(d, 2H, J=8.3Hz), 6.44(d, 2H, J=15.9Hz), 3.77(s, 6H), 3.13(t, 4H, J=6.4Hz), 3.11(s, 6H), 2.11(t, 2H, J=6.4Hz). |

Experimental Example 1

Effect of Administration on Learning and Memory-Retention Ability of Mice

Four groups of 10 mice aged 4-5 weeks, weighing 20-25 g were used in the experiment. Each sample was administered with 1% DMSO and 1% CMC using a Sonde once a day (samples: A—physiological salin solution; B—beta-amyloid; C—cinnamic acid dimer (example 1) and beta-amyloid). After injecting 1.82 g of each sample to the cerebral ventricle 3 consecutive days, passive avoidance test was conducted on the first and second day for following the last injection. All data was attained by the average of 10 mice.

In order to examine the learning and memory-retention ability of a mouse, a passive avoidance test was carried out in accordance with the method described in Song et al, *J. Neurochem.*, 1998, 71, 875. A passive avoidance chamber equipped with a light room and a dark room was prepared, wherein the floor of the dark room was designed to deliver an electrical shock to the test animal. First, a mouse was put in the light room and, upon entering the dark room, an electrical shock of 0.25 mA was given to the animal for 1 second. Twenty-four hours after the training, the mouse was put in the light room again. Then, the time it took for the mouse to enter the dark room was measured as a passive avoidance time. The maximum restriction time was set at 300 seconds, i.e., in cases where the mouse took more than 300 seconds to enter the dark room, the passive avoidance time was determined to be 300 seconds. The obtained results are shown in FIG. 1.

As can be seen in FIG. 1, the step-through latency(sec) is significantly higher for the mice (c) administered with both cinnamic acid dimer of formula 1 and beta-amyloid, than that of the mice (B) administered with beta-amyloid (1-42) only. Thus the learning and memory-retention ability for mice are excellent.

Experimental Example 2

Oral Toxicity Test of Cinnamic Acid Dimers

Twenty female and twenty male Spraque-Dawley rats aged 4 weeks were divided into four groups including 5 female and 5 male rats, after being raised in a vivarium of a temperature of 22±3° C., a relative humidity of 50±10%, an illumination of 150-300 Lux for 1 week.

The cinnamic acid dimers prepared in Example 1 were dissolved in corn oil, and the rats of the 4 groups were orally administered with the solution at a dose of 300, 1,000, 3,000 and 10,000 mg/kg once. After administration, changes of general symptoms and occurrence of death were observed for 7 days. In addition, the rats were killed on the seventh day after administration, dissected, and internal organs were examined with the unaided eye. Daily weight change was measured from the administration day and thus the weight decrease of animals attributed to cinnamic acid dimers was observed.

As a result, $LD_{50}$ values of cinnamic acid dimers were found to be 5,000 mg/kg for both males and females. All surviving animals were dissected and observed. No pathological changes were seen with the naked eye for the group administered with 5,000 mg/kg or less. In addition, the body weight of the group administered with 5,000 mg/kg or less.

Formulation Example 1

Preparation of Hard Gelatin Capsule Formulation 100 mg of the cinnamic acid dimers prepared in Example 1, 45 mg of milk calcium, 122 mg of microcrystalline cellulise, 15 mg of isoflavon, 2.5 mg of ginkgo extract, 2 mg of *Zizyphus jujuba* extract, 0.25 mg of vitamin $B_1$, 0.3 mg of vitamin $B_2$, 0.0025 mg of vitamin $D_3$ and 2.5 mg of magnesium stearate were mixed thoroughly and filled into a hard capsule to prepare a hard gelatin capsule formulation.

Formulation Example 2

Preparation of Parenteral Solution Formulation 0.03 g of cinnamic acid dimer prepared in Example 1, 0.6 g of sodium chloride and 0.1 g of ascorbic acid were dissolved in diluted water to obtain a solution of 100 ml. The solution was added to a bottle and then sterilized with heat at 20° C. for 30 minutes.

The present invention has been described in an illustrative manner, and it is to be understood that the terminology used is intended to be in the nature of description rather than of limitation. Many modifications and variations of the present invention are possible in light of the above teaching. Therefore, it is to be understood that within the scope of the appended claims, the invention may be practiced otherwise than as specifically described.

What is claimed is:

1. A cinnamic acid dimer represented by Formula 1, or a pharmaceutically acceptable salt thereof:

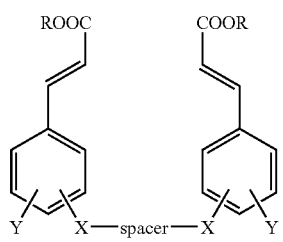

(Formula 1)

wherein, R is hydrogen or an alkyl group of $C_2$-$C_5$;
X is oxygen, —NH, or —$NCH_3$;
Y is —$NHCH_3$ or —$N(CH_3)_2$;
spacer is $C_2$-$C_8$ alkylene, $C_3$-$C_8$ alkenylene, $C_3$-$C_8$ alkylene having oxygen or $C_3$-$C_8$ alkenylene having oxygen; and
X and Y of the cinnamic acid dimer are independently in the position of meta or para.

2. A pharmaceutically acceptable salt according to claim 1, wherein said salt is an inorganic salt.

3. A method for preparing a cinnamic acid dimer represented by Formula 1, said method comprising reacting the benzaldahyde dimer compound represented by Formula 2 with malonic acid, or malonic acid ester, to obtain the cinnamic acid dimer of Formula 1:

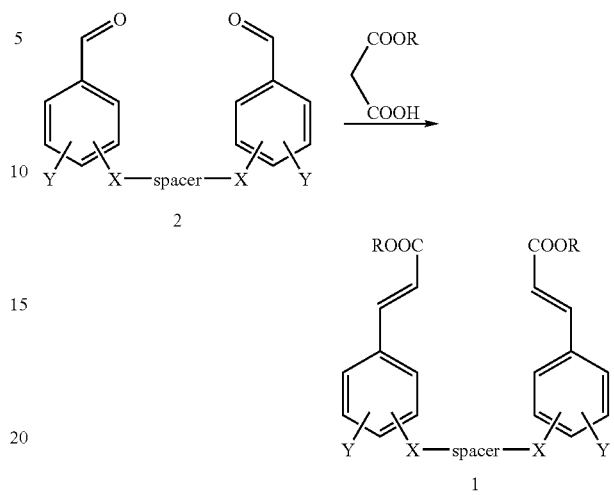

(Reaction scheme 1)

wherein, R is hydrogen or an alkyl group of $C_2$-$C_5$;
X is oxygen, —NH, or —$NCH_3$;
Y is —$OCH_3$, —$NHCH_3$ or —$(CH_3)_2$;
spacer is $C_2$-$C_8$ alkylene, $C_3$-$C_8$ alkenylene, $C_3$-$C_8$ alkylene having oxygen, or $C_3$-$C_8$ alkenylene having oxygen; and
X and Y of the cinnamic acid dimer are independently in the position of ortho, meta or para.

4. The method according to claim 3, wherein the reaction is conducted in the presence of pyridine and piperidine.

5. The method according to claim 3, wherein the reaction is conducted at 80-90° C. for 3-5 hours.

6. The method according to claim 3, further comprising reacting hydroxybenzaldehyde, or aminobenzaldehyde, with the ditosyl compound of Formula 4 in the presence of base to obtain the benzaldehyde dimer compound of Formula 2:

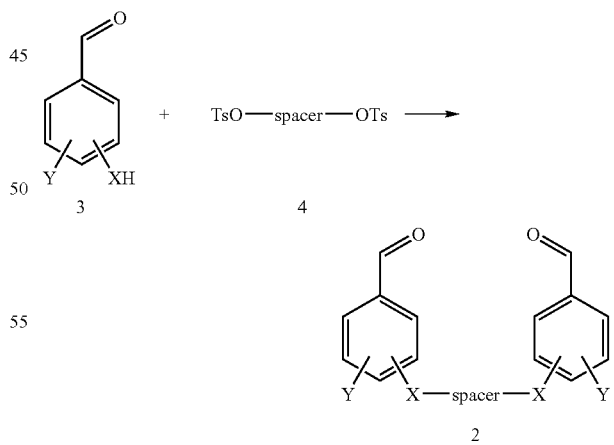

(Reaction scheme 2)

wherein, R, X, Y and spacer are defined as above Formula 1.

7. The method according to claim 6, wherein the base is LiH, NaH, Kid or NaOH.

8. A method for improving teaming and memory-retention ability in a mammal, comprising administering a therapeutically effective amount of a cinnamic acid dimer represented by Formula 1 or pharmaceutically acceptable salt thereof to the mammal:

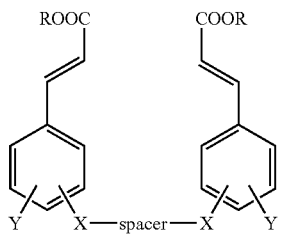

(Formula 1)

wherein, R is hydrogen and alkyl group of $C_2$-$C_5$;

X is oxygen, —NH or —NCH$_3$;
Y is —OCH$_3$, —NHCH$_3$ or —N(CH$_3$)$_2$;
spacer is $C_2$-$C_8$ alkylene, $C_3$-$C_8$ alkenylene, $C_3$-$C_8$ alkylene having oxygen or $C_3$-$C_8$ alkenylene having oxygen; and
X and Y of the cinnamic acid dimer are independently in the position of ortho, meta or para.

9. The salt according to claim 2, wherein said inorganic salt is selected from sodium salt, potassium salt, magnesium salt and calcium salt.

10. A pharmaceutically acceptable salt according to claim 1, wherein said salt is an organic salt.

11. The salt according to claim 10, wherein said organic salt is selected from angelic acid, lysine, ethanolamine and N,N'-dibenzylethylenediamine.

12. The method according to claim 8, wherein said cinnamic acid dimmer is selected from the group consisting of:

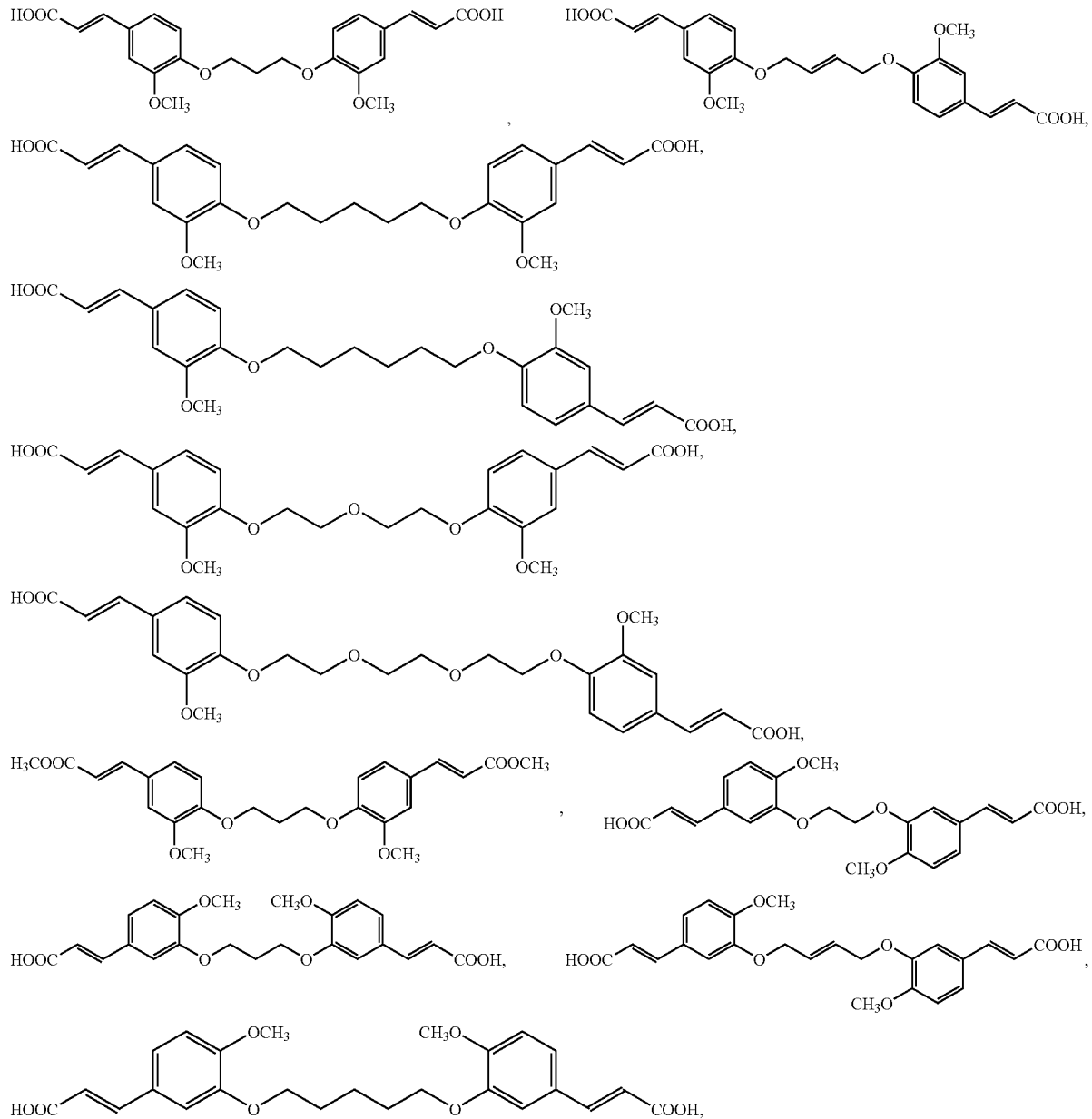

-continued
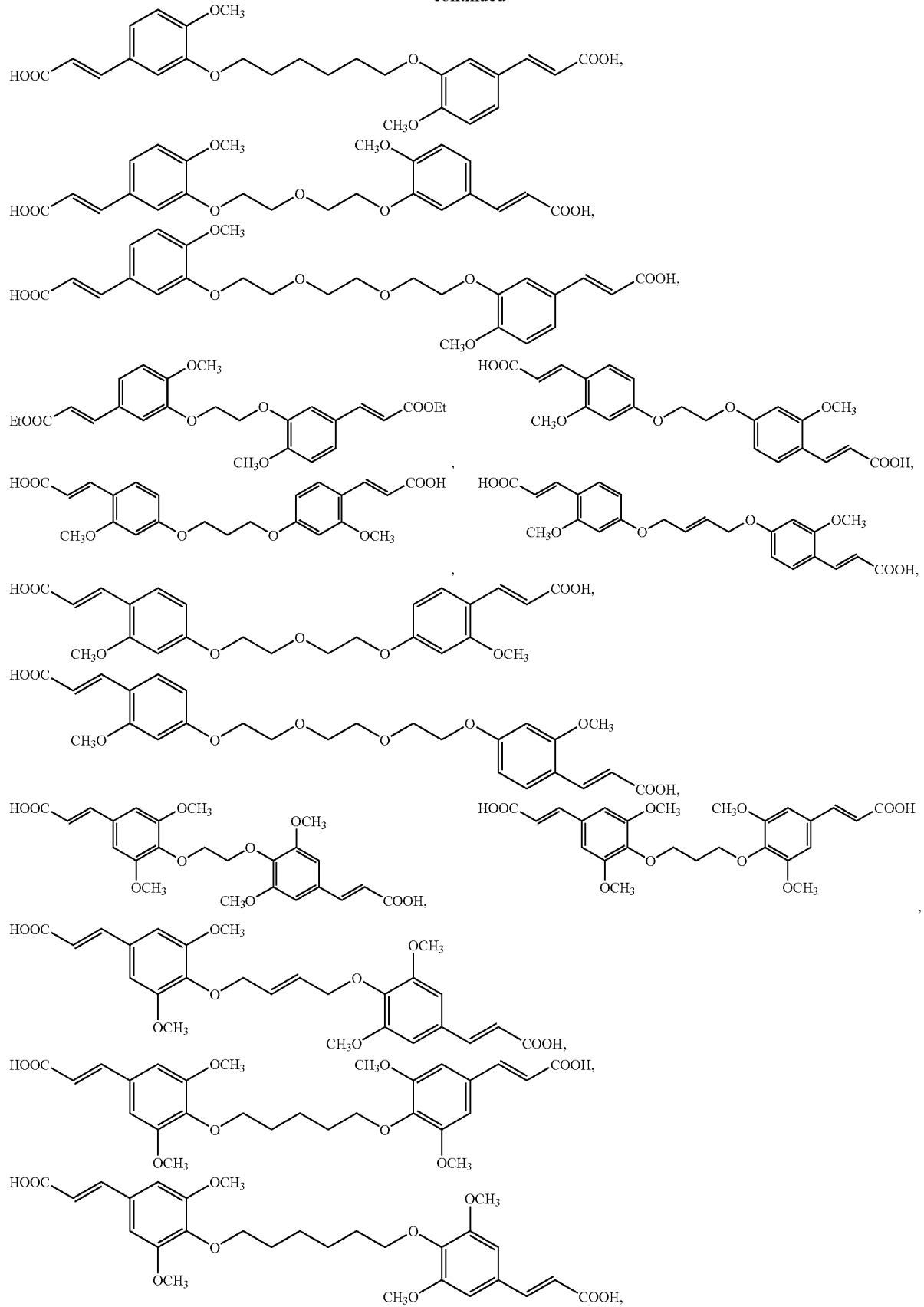

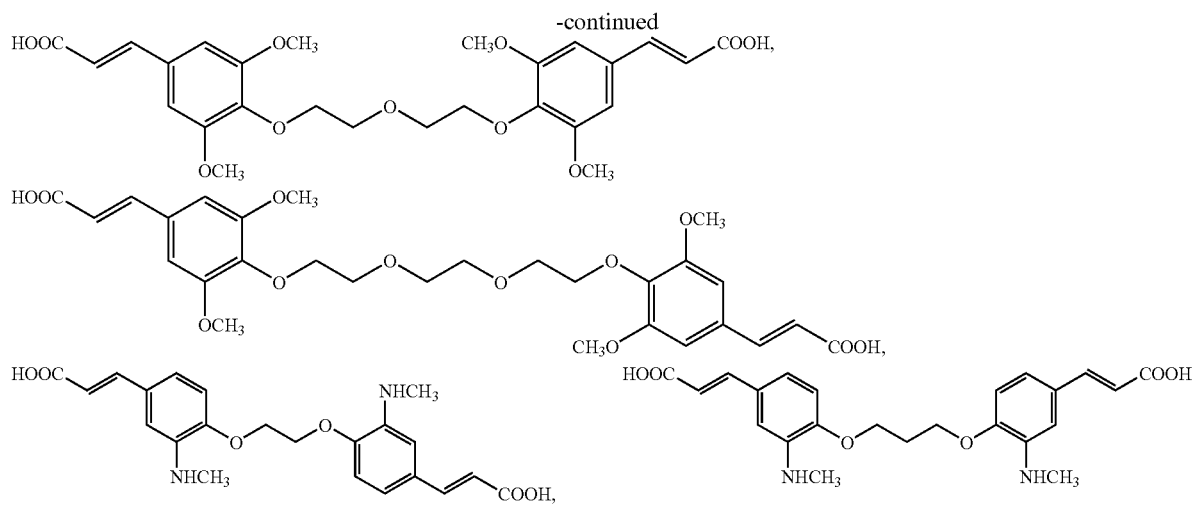
13. The method according to claim 8, wherein said cinnamic acid dimmer is 1,2-di[2-methoxy-4-(2-carboxylviny)]phenoxyethane.
14. A cinnamic acid dimer selected from the group consisting of:
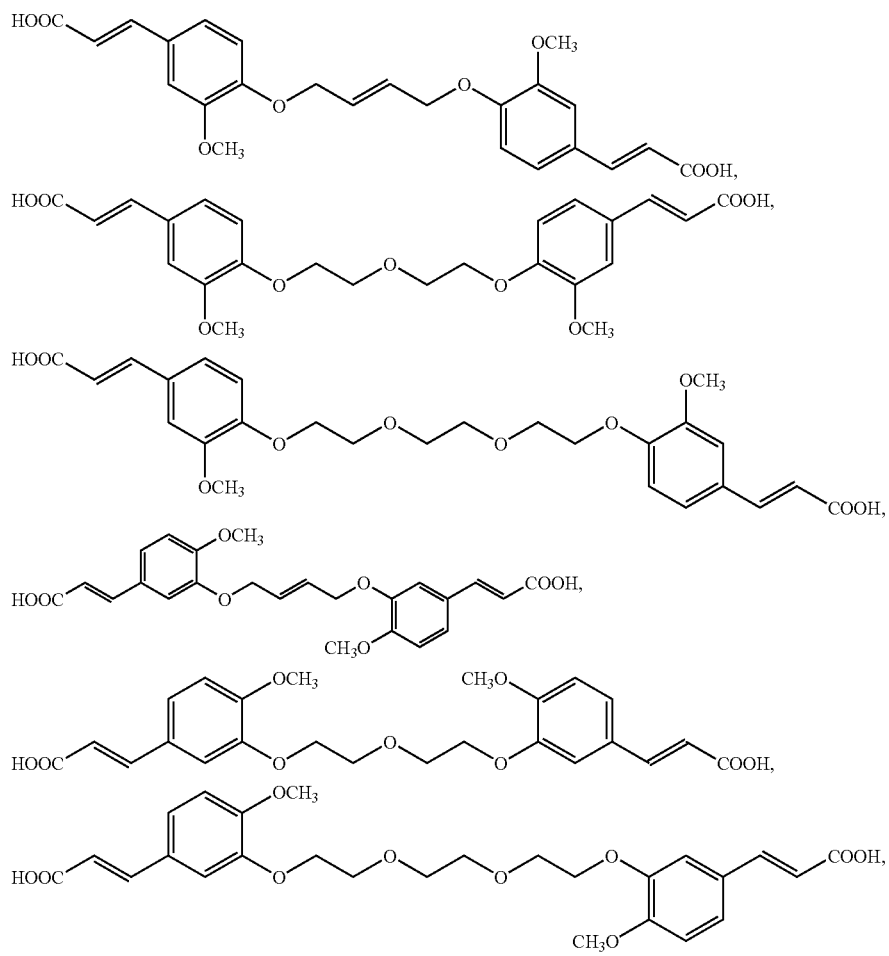

-continued
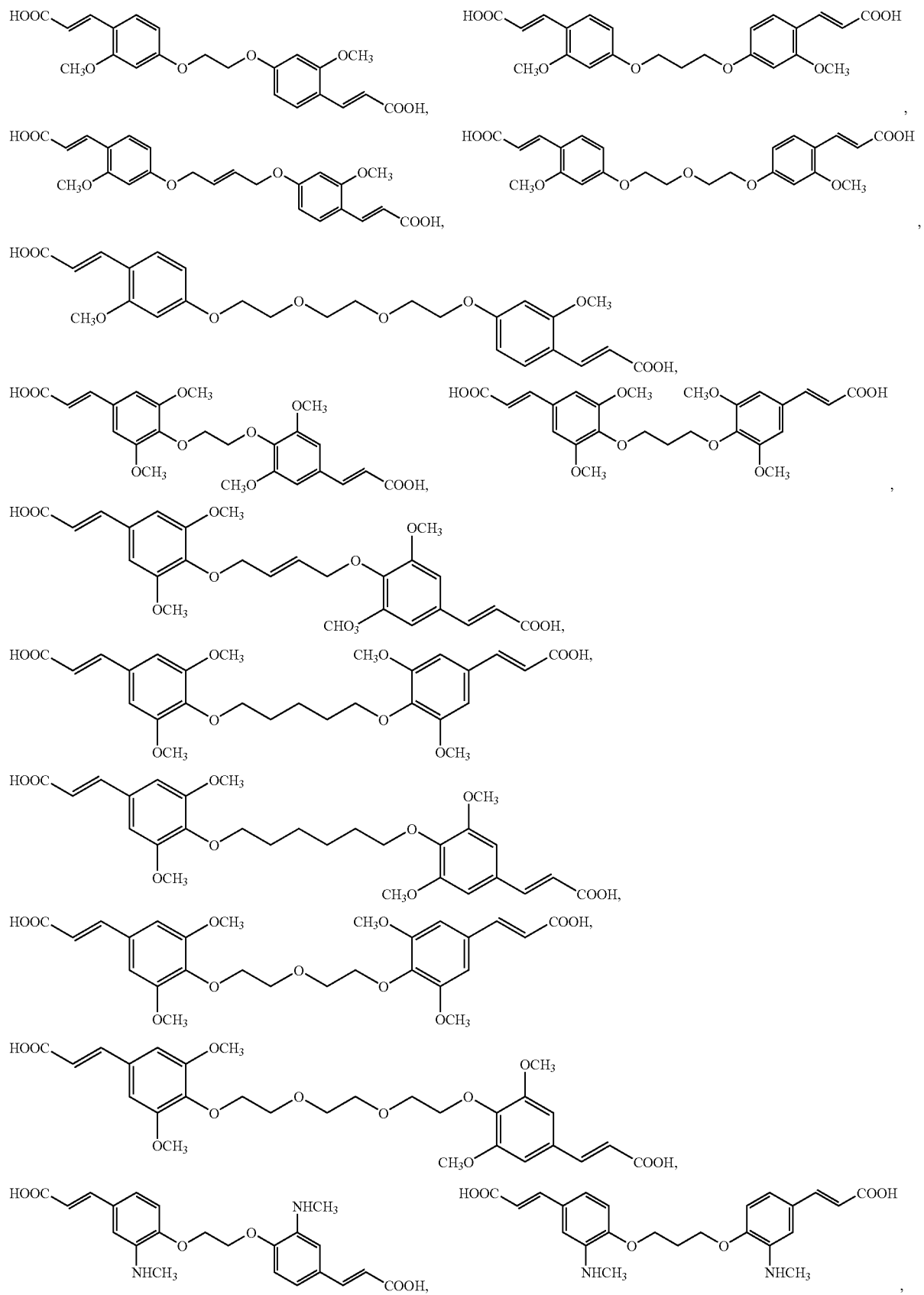

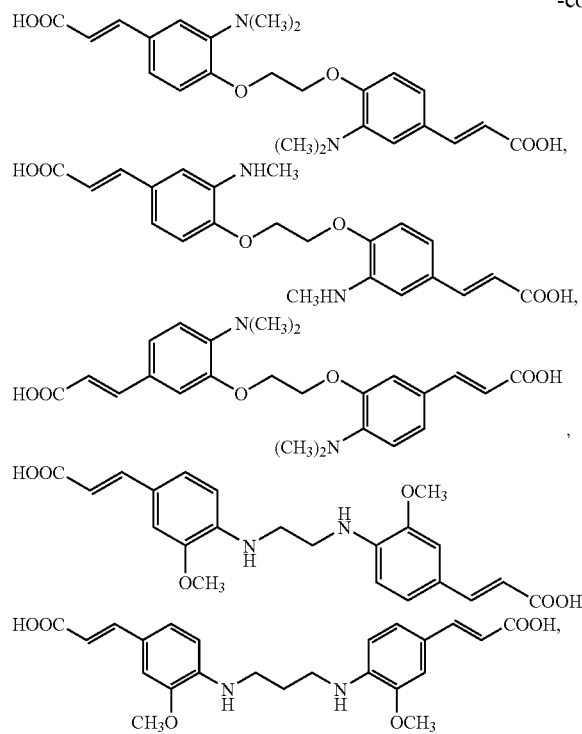
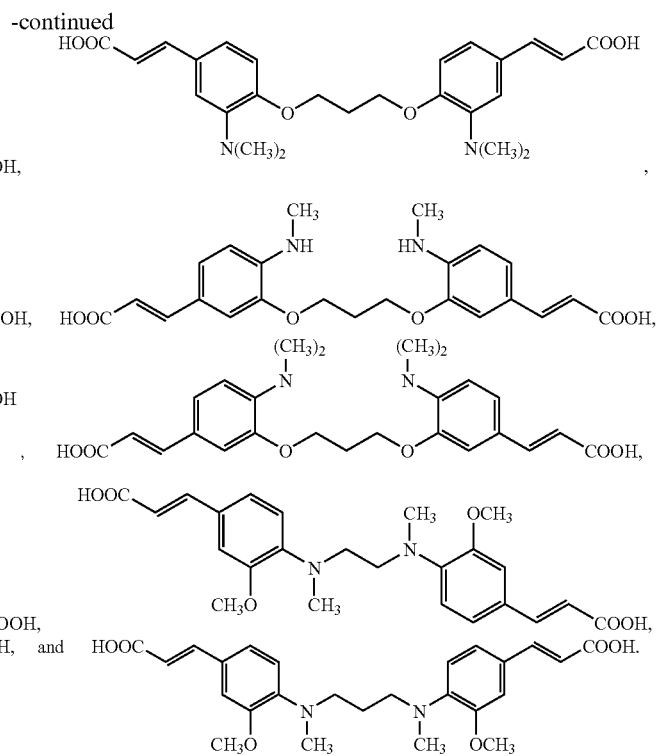
15. A cinnamic acid dimer, 1,2-di[2-methoxy-4-(2-carboxylviny)]phenoxyethane.
* * * * *